United States Patent [19]

McLoughlin et al.

[11] Patent Number: 5,498,624
[45] Date of Patent: Mar. 12, 1996

[54] SELECTED PYRAZOLYL DERIVATIVES

[75] Inventors: Jim I. McLoughlin, St. Louis; Deborah A. Mischke, Defiance; Marla J. Williams, St. Louis; Suzanne Metz, Chesterfield, all of Mo.

[73] Assignee: Monsanto Company, St. Louis, Mo.

[21] Appl. No.: 434,432

[22] Filed: May 3, 1995

[51] Int. Cl.⁶ .......................... A01N 43/56; C07D 231/14
[52] U.S. Cl. ......................................... 514/406; 548/374.1
[58] Field of Search ........................ 548/374.1; 514/406

[56] References Cited

U.S. PATENT DOCUMENTS

| 4,214,090 | 7/1980 | Huppatz . | |
|---|---|---|---|
| 4,742,074 | 5/1988 | Nishida et al. | 514/406 |
| 5,093,347 | 3/1992 | Graneto et al. | 514/406 |
| 5,223,526 | 6/1993 | McLoughlin et al. | 514/406 |

FOREIGN PATENT DOCUMENTS 4231517  3/1994  Germany .

*Primary Examiner*—Robert W. Ramsuer
*Attorney, Agent, or Firm*—Joan Thierstein; Richard H. Shear; James C. Bolding

[57] ABSTRACT

Novel azolyl derivatives, ie 2'-(substituted)cycloalkyl carboxanilides, useful as fungicides, methods of using said compounds and mixtures containing them.

7 Claims, No Drawings

SELECTED PYRAZOLYL DERIVATIVES

FIELD OF THE INVENTION

The present invention provides novel pyrazolyl substituted, particularly derivatives of cyclohexyl carboxanilides having unexpected usefulness as fungicides.

BACKGROUND OF THE INVENTION

Fungicides control various phytopathological diseases by interrupting various metabolic pathways within the fungal organism. Thus different fungicides may control the same disease, but by different modes of action. Many organisms, however, can develop resistance to a particular mode of action over time. Thus, having available fungicides which act by various modes of action is important to adequately control most diseases.

One mode of action is the inhibition of the succinate dehydrogenase (SDH) enzyme in the respiratory pathway of fungi. This mode of action has previously been demonstrated for control of basidiomycetes. For example, carboxin, is a commercially available fungicide which exhibits the SDH inhibitory mode of action against various basidiomycetes. Drouhot et al. ["*Properties of Botrytis cinerea Mitochondria and Effects of Various Toxicants Including Fungicides,*" *Pesticide Science*, 30:415–417, 1991] have suggested that such a mode of action for control of ascomycetes, such as Botrytis sp., is needed to overcome resistance problems. In their tests of respiratory inhibition, carboxin exhibited a 68% inhibition at 1 μM concentration and was judged the best fungicide of those tested for SDH mode of action against Botrytis.

Pyrazolecarboxamide fungicides are known in the art. U.S. Pat. No. 4,214,090 (Huppatz, Jul. 22, 1980) discloses various N-(phenyl)pyrazolecarboxamides. U.S. Pat. Nos. 4,742,074 (May 3, 1988, Nishida et al) and 5,093,347 (Mar. 3, 1992, Graneto et al) dis-close various N-(substituted-indanyl)pyrazole-4-carboxamides, U.S. Pat. No. 5,223,526 discloses pyrazole carboxanilides and German DE 42 31 517 discloses various heterocyclic N-(2-substituted phenyl) carboxamides useful as fungicides for various agronomic diseases.

It is an object of this invention to provide novel compounds having a high level of activity in SDH inhibition in ascomycetes. It is a further object of this invention to provide compounds having a broad spectrum of activity against fungal diseases of plants. It is a further object of this invention to provide methods of controlling or preventing fungal diseases of plants. It is a still further object of this invention to provide fungicidal compositions useful in carrying out those methods. The present inventions include surprising and unexpected advantages over previously known fungicides.

These objects are accomplished by providing a combination of substituents not heretofore appreciated including a sterically demanding group, which is a selectively substituted cyclohexyl alpha to an anilide linkage. This sterically demanding group provides a heretofore unknown advantageous effect.

SUMMARY OF THE INVENTION

Therefore, the present invention comprises compounds of the formula:

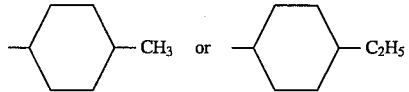

wherein:
$R_1$ is $CF_3$ and $R_2$ is

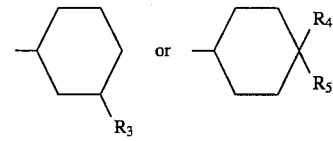

or
$R_1$ is $CHF_2$ and $R_2$ is wherein
$R_3$ is $CF_3$ or $CH_3$;
$R_4$ is $CH_3$, $C_2H_5$, $CF_3$ or $OC_2H_5$; and
$R_5$ is H or $CH_3$.

The present invention also provides methods of controlling or preventing fungal diseases of plants by applying one or more compounds as just described to the plant locus. The present invention also provides fungicidal compositions comprising one or more of the compounds just described and one or more adjuvants.

DETAILED DESCRIPTION OF THE INVENTION

Most of the compounds of the present invention may be easily prepared by coupling the desired 4-pyrazolecarbonyl chloride with the desired aniline. The following synthetic methods exemplify the ways in which the carbonyl chloride compounds and the anilines may be prepared and coupled. Other compounds of the present invention may be derived from the anilides so prepared. The following abbreviations have the meanings shown:

| | |
|---|---|
| RT | room temperature |
| RC | radial chromatography |
| h | hour(s) |
| min | minute(s) |
| DMSO | dimethylsulfoxide |
| TBF | tetrahydrofuran |
| EtOAc | ethyl acetate |
| NMP | N-methyl pyrrolidone |
| GC | gas chromatography |
| Boc | O-tert-butylcarbamoyl |
| HPLC | chromatography on silica (Waters 500 A, preparative liquid chromatograph) |

Anilines
N-Boc aniline: Phenylisocyanate (500 g) and tert-butanol (500 mL) are mixed in toluene (500 mL) in a 2 L round bottom flask. The solution is stirred over night in a 50° C. water bath. The N-Boc aniline is collected by filtration to give the white solid (702 g).

4,4-Dimethylcyclohexyl aniline.

4,4-Dimethylcyclohexyl spirobenzoxazine: To an oven-dried, three neck round bottomed flask with mechanical stirrer and addition funnel is added N-Boc aniline (0.5 19 mole) in anhydrous THF (400 mL). The solution is cooled to −70° C. t-Butyl lithium (1.24 mole, 1.7M in hexanes) is added over 40 minutes, while maintaining reaction temperature below −50° C. The reaction is stirred at −20° C. for 2.5 hours. 4,4-Dimethylcyclohexanone (1.04 mole) in THF (50 mL) is added to the reaction at −70° C. over 30 minutes. The solution is slowly warmed to RT while stirring overnight. Potassium t-butoxide (0.5 g) is added, and the reaction is heated to reflux for 2 h. The reaction is cooled to RT, and ether is added. The organic layer is washed sequentially with 2% aqueous HCl, water and brine (a saturated, or nearly saturated, aqueous salt (NaCl) solution), separated, dried over MgSO$_4$, filtered and concentrated under vacuum. Chromatography (20% EtOAc/hexanes) affords the spirobenzoxazine product as an orange solid 92.2 g (77%).

4,4-Dimethylcyclohexenylaniline: The spirobenzoxazine (0.33 mol) is heated at reflux in 9N HCl (600 mL) under N$_2$ over night. The reaction is cooled to RT. Solvent is added (CH$_2$Cl$_2$, 400 mL) and the contents of the flask are poured over ice water and neutralized with 10% NaOH to pH 9. The organic layer is washed with water, then brine, dried over MgSO$_4$, filtered and concentrated under vacuum to give a crude oil. The product is distilled (Kugelrohr) to giving the cycloalkenylaniline (46.5 g, 74%) as a yellow oil.

4,4-Dimethylcyclohexyl aniline: In a Parr hydrogenation flask, cyclohexenylaniline (46.4 g, 0.247 mol) is dissolved in 30 mL of 3:1 EtOH/AcOH and 10% Pd on carbon (0.5 g) is added. The reaction is shaken under H$_2$ (60 psi) overnight. The mixture is filtered through a pad of celite and concentrated under vacuum. The crude product is dissolved with CH$_2$Cl$_2$ and neutralized with saturated aqueous bicarbonate. The organic layer is washed with water, dried over MgSO$_4$ and concentrated to give a the 4,4-Dimethylcyclohexyl aniline as a light yellow oil (42.2 g, 90%).

Cis-2-(4'-ethylcyclohexenyl)aniline

N-Boc-2-(tributyltin)aniline: A jacketed reactor is charged with N-Boc aniline (119 g) and anhydrous ether (1 L) under nitrogen. The contents are cooled to −10° C. and t-BuLi (1.7M, 800 mL) is added dropwise so that the temperature is maintained between −10 and −2° C. After stirring 3 h at −10° C., tri-n-butyltin chloride (206 g) in ether (300 mL) is added dropwise, again maintaining the temperature below −2° C. The contents are slowly warmed to RT over 2 h, and water is carefully added. The organic materials are extracted with ether, separated and dried (MgSO$_4$). The product, N-Boc-2-(tributyltin)aniline, is filtered and concentrated to an orange oil (306 g) and used without additional purification.

N-Boc-2-(4'-ethylcyclohexenyl)aniline: To 4-ethylcyclohexanone (0.08 mole) and 2,6-di-t-butyl-4-methylpyridine (0.136 mole) in methylene chloride (200 mL), triflic anhydride (0.12 mole) is added dropwise. A white precipitate forms. The mixture is heated 5 h at reflux, cooled and stirred over night at RT. The solids are removed by filtration and the liquor is triturated with hexanes. Additional solids are removed by filtration. The filtrate is concentrated and the oil distilled on a Kugelrohr apparatus to give the enol ester as a colorless oil. The oil is chromatographed with hexanes to give the triflate as a clear oil (8.7 g).

To the triflate (0.03 mole), triphenylarsine (0.0025 mole) and tris(dibenzylideneacetone)dipalladium(0) (0.0003 mole) in N-methyl pyrrolidone (100 mL) is added N-Boc-2-(tributyltin)aniline (0.03 mole) The mixture is stirred at RT for 72 h, until GC analysis shows no further change or the triflate is consumed. The contents are partitioned between EtOAc and water. The EtOAc layer is separated and stirred with excess saturated aqueous KF (150 mL) for 30 min. The EtOAc layer is separated, dried (MgSO$_4$), filtered and concentrated. The oil is chromatographed with 5% EtOAc/hexanes to give N-Boc-2-(4'-ethylcyclohexenyl)aniline.

To N-Boc-2-(4'-ethylcyclohexenyl)aniline (0.00 11 mole) in anhydrous acetonitrile (10 mL) at 0° C. is added trimethylsilyl iodide (0.012 mole). The reaction is monitored by TLC (10% EtOAc/hexanes). After 30 min the starting material disappears. The solution is poured into water, the pH is adjusted to 7 with 10% aqueous NaOH, and the organic material extracted with ether. The ether layer is washed with saturated aqueous sodium sulfite, dried (MgSO$_4$), filtered and concentrated to a clear oil. Alternatively, the Boc protecting group is removed by stirring the protected aniline in methylene chloride with trifluoroacetic acid at RT for 2 days. The product is obtained after washing the organic layer with pH 7 buffer, separation and drying (MgSO$_4$). If necessary, the aniline is purified by column chromatography.

2-(trans-4'-ethylcyclohexyl)aniline: The 2-(4'-ethylcyclohexenyl)aniline is reduced over 10% Pd on charcoal under 50 psi hydrogen in a Parr apparatus in ethanol. After 16 h, the solution is filtered and concentrated under reduced pressure. Partially enriched cis- or trans- fractions are isolated after HPLC separation with 5% EtOAc/hexanes. The isomers, 2-(trans-4'-ethylcyclohexyl)aniline and 2-(cis-4'-ethylcyclohexyl)aniline are assigned based on coupling constants in the proton NMR at 400MHz.

The 2-(cis-3'-methylcyclohexyl)aniline and 2-(trans-3'methylcyclohexyl)aniline are prepared as described above for 2-(4'-ethylcyclohexyl)aniline from the appropriate cycloalkenylaniline. Where stereoisomer purity is indicated, the diastereomers are separated via chromatography on silica (Waters 500 A, preparative liquid chromatograph) with EtOAc and hexanes. Stereochemical assignments are based upon coupling constants in the proton NMR in CDCl$_3$.

Other 2-(substituted cyclohexyl)anilines are prepared as described above by substituting the appropriate cyclohexanone and using analogous reaction conditions. These reactions use starting materials from commercially available sources or from preparations known or analogous to those disclosed in the literature. Such anilines include, for example:

2-(4,4-dimethylcyclohexyl)aniline
2-(3-(trifluoromethyl)cyclohexyl)aniline
2-(3-methylcyclohexyl)aniline
2-(4-methylcyclohexyl)aniline
2-(4-ethylcyclohexyl)aniline
2-(4-(trifluoromethyl)cyclohexyl)aniline
2-(4-ethoxycyclohexyl)aniline
2-(4-methyl-4-ethylcyclohexyl)aniline
2-(4-methyl-4-(trifluoromethyl)cyclohexyl)aniline
2-(4-methyl-4-ethoxycyclohexyl)aniline Heterocycles 3-(Difluoromethyl)-1-methyl-1H-pyrazole-4-carboxylic add chloride:

Ethyl 3-(difluoromethyl)-1-methyl-1H-pyrazole-4-carboxylate; To ethyl 2-(ethoxymethylene)-4,4-difluoromethyl acetoacetate (132 g, prepared analogously to the 2-(ethoxymethylene)-4,4,4-trifluoromethyl acetoacetate, JACS 73, 3684, 1951) in ethanol (600 mL) at 0° C., methyl hydrazine (29 mL) in ethanol (100 mL) is slowly added dropwise. After addition is complete, the contents are heated at reflux for 2 h. Stirring continues overnight while the contents cool to room temperature. The yellow precipitate is filtered to give the pure desired product (21 g). The filtrate is concentrated in vacuo leaving a yellow oil (81.6 g). The oil is distilled (Kugelrohr 50° C., 0.025 mm) to give the N-methyl isomer of the desired pyrazole (30 g) as a yellow oil. The distillation is continued (80° C., 0.025 mm) to give additional desired product as a yellow solid (35.8 g).

3-(Difluoromethyl)-1-methyl-1H-pyrazole-4-carboxylic acid: Ethyl 3-(difluoromethyl)-1-methyl-1H-pyrazole-4-carboxylate (22.3 g)is added to a solution of sodium hydroxide (4.4 g) in methanol (200 mL). The contents are heated at reflux for 1 h, then cooled overnight while stirring. The contents are concentrated in vacuo and diluted with water. The aqueous solution is made acidic with 2N HCl and the precipitated white solid is filtered to give the desired acid (18.2 g).

3-(Difluoromethyl)-1-methyl-1H-pyrazole-4-carboxylic acid chloride 3-(Difluoromethyl)-1-methyl-1H-pyrazole-4-carboxylic acid (21 g) and oxalyl chloride (1.1 equiv) and one drop of DMF are heated at reflux for 1.5 h. The contents are concentrated in vacuo leaving the desired acid chloride as a yellow oil.

Pyrazole—Aniline Coupling

N-(2-(4,4-dimethyl)cyclohexylphenol)-1-methyl-3-(difluoromethyl)-1H-pyrazole-4-carboxamide:

To 1-methyl-3-(difluoromethyl)-1H-pyrazole-4-carboxylic acid chloride (1.6 g) in CH$_2$Cl$_2$ (25 mL) at 0° C. is added a solution of 2-( 4,4dimethyl)cyclohexylaniline (1.3 g) and triethylamine (1.0 mL) in CH$_2$Cl$_2$ (25 mL). The contents are stirred overnight, coming to room temperature. The contents are washed with water, 2N HCl (2×100 mL), dried (MgSO$_4$) and concentrated in vacuo leaving an amber foam (2.9 g). Crystallization from EtOAc/hexane gives the desired amide as white crystals (1.2 g).

The following examples of compounds of the present invention are prepared as described above using the appropriate 3-difluoromethyl- 1-methyl-5-pyrazolecarboxylic acid chloride and 1-methyl- 3-trifluoromethyl-5-pyrazolecarboxylic acid chloride under analogous reaction conditions and used in the biological assays described below.

| Example Cpd. No. | Compound Name | Melting pt. (°C.) |
| --- | --- | --- |
| 1 | 1H-pyrazole-4-carboxamide, 3-(difluoromethyl)-N-[2-(4-ethylcyclohexyl)phenyl]-1-methyl-, cis- | 127 |
| 2 | 1H-pyrazole-4-carboxamide, 3-(difluoromethyl)-1-methyl-N-[2-(-3-methylcyclohexyl)phenyl]-, cis- | 128 |
| 3 | 1H-pyrazole-4-carboxamide, 3-(difluoromethyl)-1-methyl-N-[2-(3-methylcyclohexyl)phenyl]-, trans- | 94 |
| 4 | 1H-pyrazole-4-carboxamide, 1-methyl-N-[2-(4-methylcyclohexyl)phenyl]-3-(trifluoromethyl)-, trans- | 140 |
| 5 | 1H-pyrazole-4-carboxamide, 3-(difluoromethyl)-N-(2-(4,4-dimethylcyclohexyl)phenyl]-1-methyl- | 139 |
| 6 | 1H-pyrazole-4-carboxamide, 3-(difluoromethyl)-1-methyl-N-[2-(3-trifluoromethyl)cyclohexyl)-phenyl]-,trans- | 61.0–65.0 |
| 7 | 1H-pyrazole-4-carboxamide, 3-(difluoromethyl)-N-[2-(4-ethoxycyclohexyl)phenyl]-1-methyl-,trans- | 119.0–120.0 |
| 8 | 1H-pyrazole-4-carboxamide, 3-(difluoromethyl)-1-methyl-N-[2-[4-trifluoromethyl)cyclohexyl]phenyl]- | 85.0–91.0 |

The compounds of the present invention may be used as is without adding any other components, but generally, they are formulated into emulsifiable concentrates, wettable powders, suspension formulations, granules, dusts, and the like by mixing with a solid or liquid carrier, a surface active agent and other adjuvants for formulation. The compounds of the present invention may also be microencapsulated or otherwise formulated for delayed release of activity.

The content of a compound of the present invention contained as an active ingredient in these formulations is 0.1 to 99.9%, preferably 0.2 to 80% by weight, and more preferably 2 to 50% by weight. The concentration of the active compound in the spray solutions as they are applied to growing plants will be much less, from about 10 ppm up to about 1000 ppm.

The exact amount of active ingredient per hectare to be employed in the treatment or prevention of disease is dependent upon various factors, including the plant species and stage of development of plants and disease, the amount of rainfall, and the specific adjuvants employed. In foliar applications a dosage of from about 10 to about 2000 g/ha, preferably from about 20 to about 250 g/ha, is usually employed. In soil applications a dosage of from about 100 to about 2000 g/ha, preferably from about 250 to about 500 g/ha is usually employed. Lower or higher rates may be required in some instances. One skilled in the art can readily determine from this specification, including the following examples, the optimum rate to be applied in any particular case.

The solid carders include, for example, fine powders or granules of kaolin clay, attapulgite clay, bentonite, acid clay, pyrophyllite, talc, diatomaceous earth, calcite, corn starch powder, walnut shell powder, urea, ammonium sulfate, synthetic hydrated silicon dioxide, and the like. The liquid carder includes, for example,aromatic hydrocarbons such as xylene, methylnaphthalene and the like, alcohols such as isopropanol, ethylene glycol, cellosolve and the like, ketones such as acetone, cyclohexanone, isophorone and the like, vegetable oils such as soybean oil, cotton seed oil and the like, dimethyl sulfoxide, acetonitrile, water, and the like.

The surface active agents used for emulsification, dispersion, wetting, etc, include, for example, anionic surface active agents, such as salts of alkyl sulfate, alkyl or aryl sulfonates, dialkylsulfosuccinates, salts of polyoxyethylene alkyl aryl ether phosphoric acid esters, or naphthalene-sulfonic acid/formalin condensates, etc, and nonionic surface active agents, such as polyoxyethylene alkyl ether, polyoxyethylene-polyoxypropylene block copolymers, sorbitan fatty add esters, or polyoxyethylene sorbitan fatty acid esters, etc. Other adjuvants for formulation include, for example, xanthan gum, lignosulfonates, alginates, polyvinyl alcohol, gum arabic, and CMC (carboxymethyl cellulose).

Penetrating agents, to increase systemic activity may also be added to the compounds of the present invention. When used in plant protection, a compound according to the invention or mixtures thereof, as such or in their formulations, can also be used in the form of mixture with other active ingredients, for example, herbicides, bacteriocides, acaricides, nematocides, insecticides, growth regulators, and other fungicides, and may furthermore be mixed and applied together with fertilizers. The mixtures are advantageous, for example to broaden the spectrum of action or to prevent the build-up of resistance. In some cases, synergistic effects are observed, which means that the activity of the mixture is greater than the total of the activities of the individual components.

Examples of fungicides which may be combined with the novel compounds are: 2-aminobutane; 2-anilino-4-methyl-6-cyclopropylpyrimidine; 2',6'-dibromo- 2-methyl-4'trifluoromethoxy-4'-trifluoromethyl-1,3-thiazol-5-carboxanilide; 2,6-dichloro-N-(4-trifluoromethylbenzyl)benzamide; (E)-2-methoxyimino-N-methyl-2-(2-phenoxyphenyl)acetamide; 8-hydroxyquinoline sulphate; methyl (E)-2-{2-[6-(2-cyanophenoxy)pyrimidin- 4-yloxy]phenyl]-3-methoxyacrylate; methyl (E)-methoximino{alpha(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazole, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fiuquinconazole, flusilazole, flusulfamide, flutolanil, flutriafol, folpet, foxetyl-aluminium, fthalide, fuberidazole, furalaxyl, furmecyclox, guazatine, hexachlorobenzene, hexaconazole, hymexazole, imazalil, imibenconazole, iminoctadine, iprobenfor (IBP), iprodione, isoprothiolane, kasugamycin, copper preparations, such as: copper hydroxide, copper naphthenate, copper oxychloride, copper sulphate, copper oxide, oxine copper and Bordeaux mixture, mancopper, mancozeb, maneb, mepanipyhrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, perfurazoate, penconazole, pencycuron, phosdiphen, pimaricin, piperalin, polyoxin, probenazole, prochloraz, procymidone, propamocvarb, propiconazole, propineb, pyrazophos, pyrifenox, pyrimethanil, pyroquilon, quintozen (PCNB), sulphur and sulphur preparations, tebuconazole, tecloftalam, tecnazen, tetraconazole, thibendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram.

Examples of bactericides which may be combined with the novel compounds of the present invention are:

Bronopol, dichlorophen, nitrapyrin, nickel dimethyldithiocarbamate, kasugamycin, octhilinon, furanecarboxylic acid, oxytetracyclin, probenazole, streptomycin, tecloftalam, copper sulphate and other copper preparations.

Examples of insecticides, acaricides and nematicides which may be combined with the novel compounds of the present invention are:

Abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, betasyluthrin, bifenthrin, BPMC, brofenprox, bromophos A, bufencarb, buprofezin, butocarboxin, butylpyridaben, cadusafox, carbaryl, carbofuran, carbophenothion, carbosulphan, cartap, CGA 157 419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethione, diflubenzuron, dimethoate, dimethylvinphos, dioxathion, disulphoton, edifenphos, emamectin, esfenvalerate, ethiofencarb, ethione, ethofenprox, ethoprophos, etofenprox, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidaclopid, iprobenfos, isazophos, isofenphos, isoprocarb, isoxathione, ivemectin, lambda-cyhalothrin, lufenuron, malathion, mecarbam, meavinphos, mesulphenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin,phenthoate, phorate, phosalone, phosmet, phospham; don, phoxim, pirimicarb, propaphos, propoxur, prothiofos, prothoate, pymetrozin, pyrachlophos, pyradaphenthion, pyresmethrin, pyrethrum, pyridaben, pyrimidifen, pyriproxifen, quinalphos, RH 5992, salithion, sebufos, silafluofen, sulphotep, sulprofos, tebufenozid, tebufenpyrad, tebupirimiphos, teflub enzuron, tefluthrin, temephos, terbam, terbufos, tetrachlorvinphos, thiafenox, thiodicarb, thiofanox, thiometon, thionazin, thuringiensin, tralomethrin, triarathen, triazophos, triazuron, trichlorfon, triflumuron, trimethacarb, vamidathio, XMC, xylylcarb, zetamethrin.

Fungicides of the present invention are employed in plant protection for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation:

Monilia species, such as fructicola;

Uncinula species, such as necator;

Rhizoctonia species, such as solani;

Xanthomonas species, such as Xanthomonas;

Pseudomonas species, such as *Pseudomonas lachrymans*;

Erwinia species, such as *Erwinia amylovora*;

Pythium species, such as *Phthium ultimum*;

Phytophthora species, such as *Phytophthora infestans*;

Pseudoperonospora species, such as *Pseudoperonospora humuli* or *Pseudoperonospora cubensis*;

Plasmopara species, such as *Plasmopara viticola*;

Peronospora species, such as *Peronospora pisi* or *P. brassicae*;

Erysiphe species, such as *Erysiphe graminis*;

Sphaerotheca species, such as *Sphaerotheca Fuliginea*;

Podosphaera species, such as *Podosphaera leucotricha;*

Venturia species, such as *Venturia inaequalis;*

Pyrenophora species, such as *Pyrenophora teres* or *P. graminea* (conidia form: Drechslera, syn: Helminthosporium);Cochliobolus species, such as *Cochliobolus sativus* (conidia form: Drechslera, syn: Helminthosporium);

Uromyces species, such as *Uromyces appendiculatus;*

Puccinia species, such as *Puccinia recondita;*

Tilletia species, such as *Tilletia caries;*

Ustilago species, such as *Ustilago nuda* or *Ustilago avenae;*

Pellicularia species, such as *Pellicularia sasakii;*

Pyricularia species, such as *Pyricularia oryzae;*

Fusarium species, such as *Fusarium culmorum;*

Botrytis species, such as *Botrytis cinerea;*

Septoria species, such as *Septoria nodorum;*

Leptosphaeria species, such as *Leptosphaeria nodorum;*

Cercospora species, such as *Cercospora canescens;*

Alternaria species, such as *Alternaria brassicae* and

Pseudocercosporella species for example, *Pseudocercosporella herpotrichoides.*

Crops on which the compounds may be used include, but are not limited to, cereals, for example, wheat, rye, barley, and rice; fruits, for example, apples and grapes; vegetables, for example, eggplants, cucumbers, and tomatoes; oil-producing crops, for example, peanuts, soybeans, and oilseed rape; and turf. Application methods to be used in fungal control on plants include, but are not limited to, direct application to the body of the plant by spraying or other direct application means; soil treatment prior to or at the time of planting, or at any time during the life of the plant; and application to the seed or seed pieces prior to or at the time of planting. The latter two means expose the rhizosphere of the plant to the treatment compound.

The compounds of the present invention have been tested for fungicidal effectiveness in a variety of tests. They have demonstrated exceptionally high levels of control of ascomycete disease such as Septoria as demonstrated in an enzyme inhibition test as well as in vivo tests. The compounds have been compared to carboxin which is Compound No. 12 of U.S. Pat. No. 4,214,090 (Huppatz, Jul. 22, 1980) incorporated by reference therfor. U.S. Pat. No. 5,223, 526 (McLoughlin and Metz, Jun. 29, 1993 ) is believed to be the closest prior art and can be compared to this known fungicide, N-(2-methylphenyl)-1,3,5-(trimethyl)- 4-pyrazolecarboxamide, as a standard. The following examples describe the tests conducted and the results thereof.

EXAMPLE 1

Barley Powdery Mildew Foliar Assay Methods (BPM Prot)

A) Pathogen/Inoculum Production—Leaf material infected with the barley powdery mildew fungus, *Erysiphe graminis* f. sp. *hordei*, is maintained continuously on barley seedlings, cv. Perry.

B) Host Propagation—Barley seedlings, cv. Perry, are grown to second leaf stage in a commercial soil preparation, "Metro Mix 200", amended with 100 gm/ft$^3$ slow release "Osmocote 14-14-14". A sufficient number of seeds are planted per pot (5 cm in diameter) in order to insure the production of 3–5 vigorous seedlings per pot. The plants are maintained in a growth chamber set at 21° C., 80% RH with a 12 hour photoperiod. Light intensity is set at 300 me/m$^2$/sec.

C) Test Compound Preparation

1) Experimental compounds—Each or the compounds of the present invention are applied at 500, 100, and 20 ppm. Formulation is generally in 20% acetone, 59.95% water, and 0.05% Tween 20. Four pots (with 3–5 plants/pot) at each rate are treated. The application volume is 8 ml per treatment. Formulated materials, such as commercially available products, are brought up to the appropriate treatment volume with water containing Tween®20, 05% v/v.

2) Controls and standards—The commercial standards used are Corbel® (active ingredient fenpropimorph) and NUSTAR® (active ingredient flusilazole), both at the rate of 20 and/or 10 ppm. A set of control plants, treated with the formulation blank and inoculated, are also included.

D) Compound Application—Compound is sprayed onto the leaves of the plants (pots positioned on a rotating table) using a DeVilbiss Model 152 hand sprayer. Coverage of the first leaf is essential. After the plants have thoroughly dried they are returned to the growth room and randomized.

E) Inoculation/Incubation—Inoculation of the test plants takes place 24 hours after compound application. Inoculation is accomplished by gently shaking plants previously infected with the *Erysiphe graminis* f. sp. *hordeii* fungus over the test plants. This process liberates a cloud of spores which effectively and uniformly fall onto the test plants. After inoculation the plants are returned to the environmental conditions under which they were grown.

F) Evaluation—The test is assessed 6–7 days after inoculation. Treatments are evaluated by visually estimating the percentage of the leaf area infected on the first leaf. Three ratings are made on each pot (replicate). Phytotoxicity and growth effects are also noted at this time.

G) Data—All replicate data is recorded as a percent disease value. Treatment means are calculated and percent disease control is determined by the formula: (control mean—treatment mean)*100/control mean. The inoculated control treatment mean is used for this calculation. The percent protection values for the compounds of the present invention are as set out in the Table below.

EXAMPLE 2

Wheat Powdery Mildew Foliar Assay Methods (WPM Prot)

A) Pathogen/Inoculum Production—Leaf material infected with the wheat powdery mildew fungus, *Erysiphe graminis* f. sp. *tritici*, is maintained continuously on wheat seedlings, cv. Caldewell.

(B) Host Propagation, (C) Compound Preparation and (D) Compound Application follow as per Example 1.

(E) Inoculation/Incubation—Inoculation of the test plants takes place 24 hours after compound application. Inoculation is accomplished by gently shaking plants previously infected with the *Erysiphe graminis* f. sp. *tritici* fungus over the test plants. This process liberates a cloud of spores which effectively and uniformly fall onto the test plants. After inoculation the plants are returned to the environmental conditions under which they were grown.

(F) Evaluation and (G) Data follow as per Example 1. The percent protection values for the compounds of the present invention are as set out in the Table below.

EXAMPLE 3

Wheat Powdery Mildew—Foliar Curative Treatment (WPM Cur)

A) Pathogen/Inoculum Production follow as per Example 2. (B) Host Propagation, (C) Compound Preparation and (D) Compound Application follow as per Example 1.

E) Inoculation/Incubation—Inoculation is accomplished as per Example 1, 48 hours prior to compound application. The incubation period is temporarily interrupted for chemical treatment, the plants are allowed to dry and then returned to the incubation chamber.

(G) Evaluation and (H) Data follow as per Example 1. The percent protection values for the compounds of the present invention are as set out in the Table below.

EXAMPLE 4

Wheat True Eyespot In Vitro Assay Methods (WES - In Vitro)

A) Pathogen/Inoculum Production—A mycelial transfer of *Pseudocercosporella herpotrichoides* var. *tritici* is placed onto potato dextrose agar plates and allowed to grow for 40 days at 20 ° C., without light. Five agar discs are taken from the actively growing culture and are placed equidistant, mycelial side down, onto a water agar plate, and incubated at 10 ° C. with 10 hours of fluorescent light per day. After 5 days of incubation, sporulation on the transferred discs begins, and plates are flooded with 3–5 mls sterile deionized water. One-half ml aliquots are taken from the resulting spore suspension and placed on new water agar plates. Spores are spread across plates using a bent glass rod and incubated at 10 ° C. with 10 hour fluorescent light periods per day. In 5–10 days, a lawn of spores is produced and can be "harvested".

B) Compound Preparation and Test Execution—200 μl of ¼ strength potato dextrose broth is placed in each well of a 96 well microtiter plate. An appropriate amount of the compounds of the present invention are dissolved in 10 μl of acetone and added to a well to achieve a final well concentration and hence test rate of 5.0, 0.5, and 0.1 ppm per compound. The commercial standard used is prochloraz at equivalent rates.

C) Inoculation/Incubation—50 μl of a $1 \times 10^6$ spores/ml suspension harvested using the method above is added to each well. The 96 well plates are incubated for 3 days at 19° C. in the dark.

D) Evaluation—After incubation, each well is visually assessed for growth inhibition on the following 0–3 scale:
0=no inhibition of mycelial growth
1=slight inhibition of mycelial growth
2=moderate inhibition of mycelial growth
3=strong inhibition of mycelial growth The results of this test for compounds of the present invention are as set out in the Table below.

EXAMPLE 5

Wheat True Eyespot—Foliar Protectant Treatment (WES Prot)

A) Pathogen/Inoculum Production—Follows as per Example 4.

B) Host Propagation—Wheat seedlings, cv. Hart, are grown to the third leaf stage in a commercial soil preparation, "Metro Mix 200", amended with 100 gm/ft$^3$ slow release "Osmocote 14-14-1438 . A sufficient number of seeds are planted per pot (5 cm in diameter) in order to insure the production of 5 vigorous seedlings per pot. The plants are maintained in a growth chamber set at 21° C., 80% RH with a 12 hour photoperiod. Light intensity is set at 300 me/m$^2$/sec.

C) Test Compound Preparation
1) Experimental compounds—Follows as per Example 1.
2) Controls and Standards—The commercial fungicide, prochloraz, applied at 20 and 5 ppm, is used as the standard for wheat eyespot control. Control treatments are sprayed only with the formulation solution.

D) Compound Application—Wheat plants are sprayed at the three leaf stage. The solution is foliarly applied to the basal stem area of the wheat using a Devilbiss Model 152 hand sprayer. The treated wheat is allowed to air dry at room temperature before being returned to a growth chamber. The growth chamber is set at 15° C., 85% RH and a 12 hour photoperiod. Light intensity is maintained at 300 me/m$^2$/sec.

E) Inoculation/Incubation - The treated wheat plants are inoculated 24 hours after chemical treatment. Inoculation is done by spraying a $3 \times 10^5$ spores/ml suspension at the basal stem area of each plant. Approximately 1 ml of spore suspension is applied to each plant. Following inoculation, the basal stem area of the plants are covered with a 2–3 cm thick layer of fine vermiculite. The vermiculite is watered lightly and the plants returned to the growth room. The inoculated plants remain in the growth chamber for 4 weeks after which time they are evaluated for disease control.

F) Evaluation—Treatments are evaluated four weeks after inoculation. Disease assessment is based on the percent girdling of the stem base caused by an eyespot lesion. Five plants are rated per replicate. Phytotoxicity and growth effects are also noted at this time.

G) Data—All replicate data is recorded as a percent disease value. Treatment means are calculated and percent disease control is determined by the formula: (control mean—treatment mean)*100/control mean. The inoculated control treatment mean is used for this calculation. The percent protection values for the compounds of the present invention are as set out in the Table below.

EXAMPLE 6

Enzyme Inhibition—I-50 (WGB)

Succinate Dehydrogenase Assay using *Septoria nodorum* mitochondria—*Septoria nodorum* mycelia are prepared from spores via shake culture for 40–48 hours in 3% malt extract at room temperature. The mycelia are harvested by centrifugation and the pellets obtained are stored in the −80° C. freezer until use.

Mitochondria are isolated by a method adapted from White (*Biochem. Biophys. Res. Commun.* 44 (1971) 1212–19). Fifteen to twenty grams of frozen mycelia are resuspended in a 250 mL medium containing 0.25M sucrose, 5 mM tetrasodium ethylenediamine tetraacetic acid ($Na_4EDTA$), pH 7.0 containing 1.5 g/liter bovine serum albumin (BSA) and placed in a Bead Beater chamber (BioSpec Products, Bartlesville, Okla.). Zirconium oxide beads (0.5 mm) are added to finish filling the chamber. Four 30s beats separated by 2 rain temperature equilibration periods on ice are used to break the mycelia. The homogenate is centrifuged for 20 min at 3000×g and 4° C. to remove debris. The supernatant is recentrifuged at 20,000×g for 20 min at 4° C. The resulting pellet is resuspended in BSA-free sucrose/EDTA medium (40 mL) using a glass tissue homogenizer and teflon pestle and recentrifuged at 27,000×g for 15 min at 4° C. The pellet is resuspended in BSA-free sucrose/EDTA medium (~3 mL) and used for SDH assays.

The enzyme activity is measured at 600 mm in a solution containing 50 mM potassium phosphate, $pH_{7.2}$; 1 mM potassium cyanide; 45 μM 2,6-dichlorophenol indophenol (DCPIP) and 17 mM disodium succinate in a final volume of 1 mL with a Perkin-Elmer Lambda 7 ultraviolet-visible spectrophotometer. The test compounds are added as acetone solutions (final concentration of acetone less than or equal to 1%(v/v)). The mitochondrial preparations are used to initiate the reaction. All rates are corrected for succinate-independent dye reduction. Semilog plots of percentage inhibition versus test compound concentration are used to determine inhibition expressed as $I_{50}$ (μM) which is the concentration required to inhabit the rate of DCPIP reduction by 50%. The commercial fungicide carboxin is used as a standard throughout [$I_{50}$ (μM)=5.0±2.2; n=52].

The results of this assay for the compounds of the present invention are reported in the Table below.

EXAMPLE 7

Wheat Glume Blotch (WGB)—In Vitro

A) Pathogen/Inoculum Production—The wheat glume blotch fungus, *Septoria nodorum*, is cultured on yeast/malt agar at 22° C. and 12 hours fluorescent light. Several sterile loops full of mature pycnidia produced on a 7 day old culture plates are added to 30 mls of ¼ strength potato dextrose broth. After 15 minutes the suspension is stirred, and adjusted to a concentration of $3 \times 10^5$ spores/mi.

B) Compound Preparation and Test Execution—200 μl of ¼ strength potato dextrose broth is placed in each well of a 96 well microtiter plate. An appropriate amount of the compounds of the present invention is dissolved in 10 μl of acetone and added to a well to achieve a final well concentration and hence test rate of 5.0, 0.5, and 0.1 ppm per compound. The commercial standard used is flusilazole, at equivalent rates.

C) Inoculation/Incubation—50 μl of a $3 \times 10^5$ spores/ml suspension obtained using the method above is added to each well. The 96-well plate is incubated for 4–6 days at 25° C., 12 hours fluorescent light.

D) Evaluation—After incubation, each well is visually assessed for growth inhibition on the following 0–3 scale:
0=no inhibition of mycelial growth
1=slight inhibition of mycelial growth
2=moderate inhibition of mycelial growth
3=strong inhibition of mycelial growth The results of this test for compounds of the present invention are as set out in the Table below.

EXAMPLE 8 and EXAMPLE 9

Wheat Glume Blotch Foliar Assay Methods [WGB Prot (EXAMPLE 8) and WGB Cur (EXAMPLE 9)]

A) Host Propagation—Winter wheat plants, cv. Caldwell, are grown in 5.7 $cm^2$ pots, three per pot, and maintained in a growth chamber set at 20° C., 80% RH with a 12 hour photoperiod.

B) Compound Preparation—A 1.0% stock solution of each of the compounds of the present invention is first prepared utilizing an appropriate solvent such as acetone, water or DMSO. This stock is then used to prepare the final spray solution which contains the compound at the desired dosage, eg 100 ppm and 20 ppm, acetone at 20% v/v, Tween®20 at .05% w/v, and water at about 80%. Commercial standard used is tebuconazole at equivalent rates.

C) Compound Application, Seedlings are sprayed at the two-leaf stage (GS 12) using a DeVilbiss Model 152 hand operated sprayer set at 15–20 psi. Six ml of the test solution per treatment are applied to three pots. In the protectant assay (EXAMPLE 8), the compound application is made two days pre-inoculation. In the curative assay (EXAMPLE 9), the compound is applied during a brief interruption of the disease incubation period two days post-inoculation.

D) Pathogen Production/Inoculation—The wheat glume blotch fungus, *Septoria nodorum*, is maintained in the pycnidial state on yeast malt agar (YMA) and transferred weekly by streaking a suspension of conidia obtained from a ten to twelve day old sporulating culture onto fresh YMA plates. The plates are incubated at 20° C. with a 12 hour photoperiod.

Test inoculum is prepared by flooding seven day old culture plates with deionized water amended with Tween®20 (0.1% v/v) and gently scraping the pycnidia to release the extruding masses of conidia. The resulting spore suspension is filtered through two layers of cheese cloth and adjusted to $4 \times 10^6$ spores/ml utilizing the Tween®20 solution.

Forty-eight hours after the compound application and prior to inoculation, the test plants are preconditioned for at least one hour in a dark growth chamber set at 20° C. and 100% RH. After the preconditioning period is over, the conidial suspension is applied to run-off using a DiVilbiss hand operated sprayer. The plants are then returned to the preconditioning chamber and incubated at the same settings for 96 hours. Light is supplied to the plants during the last twelve hours of incubation. At the end of the 96 hour period, the plants are returned to the environmental conditions under which they were grown.

E) Test Evaluation—Eight to ten days after removal from the high humidity chamber, or twelve to fourteen days after inoculation, treatments are evaluated by visually estimating the percentage of the leaf area (on the first leaf) covered with lesions. Three ratings are made on each pot which constitutes a replicate. Each replicate then receives a numerical mean by averaging the three values. Percent disease, as well as percent control values are calculated. The percent control values obtained from these assays for the compounds of the present invention are as set out in the Table below.

EXAMPLE 10

Wheat Leaf Rust Foliar Assay Methods (WLR Prot)

A) Pathogen/Inoculum Production—Urediospores of previously infected plants are collected using a small vacuum device and stored in glass vials at −2° C. Just before inoculation the requisite number of vials are warmed and the spores suspended in Soltrol, a light machine oil.

(B) Host Propagation, (C) Compound Preparation and (D) Compound Application follow as per Example 1.

E) Inoculation/Incubation—To inoculate the plants, the urediospore/Soltrol suspension, adjusted to $5 \times 10^4$ spores/ml, is applied in a light coating to the foliage, and the plants are placed in a mist tent for 12 to 18 hours at 20° C. in the dark. The test can then be returned to the previous growing conditions until foliar symptoms are evident and the plants can be assessed.

F) Test Evaluation—About 7 days after the plants are removed from the mist tent, the rust lesions should be evident. Three leaves in each pot (replicate) are assessed for percent infection. Phytotoxicity and growth effects are also noted at this time.

G) Data—Follows as per Example 1.

EXAMPLE 11

Vine Grey Mold on Berries (VGM Prot)

A) Pathogen/Inoculum Production—The grey mold fungus, *Botrytis cinerea*, is cultured on PDA at 20° C. and 12 hours fluorescent light until the radial growth is slightly less than the plate diameter. A $1 \times 10^6$ spore/ml suspension in sterile water (0.05% Tween®20) is made by dislodging spores in a flooded plate, filtering out mycelium, and adjusting the concentration.

B) Host Preparation—Thompson or Red Flame seedless table grapes from local grocery stores are used. Grapes are washed first in room temperature soapy water solution (a few drops of detergent per gallon), and then surfaced sterilized in 70% ethanol for one minute, followed by two rinses in sterile water. Berries are chosen which still have stem (pedicel) attached.

C) Compounds
1) Experimental compounds—Each of the compounds of the present invention are applied at 200, 50, and 20 ppm. Formulation is generally in 40% acetone, 59.95% water, and 0.05% Tween®20. Replication is 6 berries per treatment. Compound is pipetted onto berries at 1.0 ml/treatment (6 berries) in a sterile petri plate. After drying, each berry is transferred to an individual well in a 12-well tissue culture plate. Formulated materials, such as commercial preparations are generally applied using the formulation only (no acetone or surfactant added).
2) Controls and Standards—Three technical grade commercial standards are used, usually at 200 and 50 ppm; benomyl, iprodione, and vinclozolin. The test controls include a uninoculated, formulation treated set as well as an inoculated, formulation treated set.

D) Inoculation/Incubation—Each berry is inoculated with 0.2 ml of spore suspension, using a sterile pipet. Incubation is in the 12-well culture plates at 20° C., 12 hour photoperiod.

E) Test Execution—One day protectant—Berries are inoculated as described 24 hours after chemical treatment.

F) Evaluation— The test is rated 7–10 days after inoculation. Percent surface area infected with disease is determined for each replicate using the values of 0, 1, 2, 5, 10, 15, 20, 25, etc. through 100%. Treatment means are calculated and percent disease control is determined by the formula "(control mean—treatment mean)*100/control mean". The untreated/inoculated control treatment is used for this calculation. The resultant percent protection or percent disease control values for the compounds of the present invention are as set out in the Table below.

EXAMPLE 12

Vine Grey Mold on Berries (VGM Cur)—Assay is as set out above in EXAMPLE 11 except for step E) which is:

Test Execution—In the curative test the berries are first inoculated as described, six per petri plate and placed in incubation. After 24 hours, the berries are temporarily removed from incubation, placed into 12-well tissue culture plates (one per well), treated, and then returned to incubation.

EXAMPLE 13

Vine Powdery Mildew Foliar Assay (VPM Prot)

A) Pathogen/Inoculum—Vine powdery mildew, caused by *Uncinula necator*, is an obligate parasite and must be maintained on a living host. Seedling leaves (2–5 leaf stage) of Vitis vinifera var. Carignane, are inoculated by brushing them with the leaves of infected plants. Incubation environment is the same as that described for incubation (Sec. D).

B) Host Propagation- Approximately 60 gm of seed are removed from cold storage and soaked in water for 2–3 days with frequent (3 or more) water changes each day. They are then combined with 24 gm of vermiculite and 30 ml of distilled water and put into refrigeration for 4–5 weeks. After this 'vernalization' period, they are planted, 3 seeds/pot, into individual 2.25" pots filled with a commercial potting mix. The pots are watered well, and placed into a growth chamber set at 24° C., 85% RH and a 12 hour photoperiod at 200–300 me/m²/ sec. The seedlings are thinned to one seedling/pot approximately 14 days after planting. After four to five additional days, seedlings are moved to the greenhouse. Plants are ready for assay 4–6 weeks after planting.

C) Test Compound Preparation

1) Experimental compounds—A final formulation of each of the compounds of the present invention in 20% acetone, 0.1% Tween®20 and 79.9% water is foliarly applied to the seedling vines at about 1.5 mls/pot (4 pots/treatment) using a DeVilbiss 152 sprayer at the rate of 100, 20 and 10 ppm. The seedlings have 2–4 true leaves at application. Treated pots are allowed to dry in a vented room and are then moved to the inoculation growth chamber (see Sec. D for settings).

2) Controls and standards—The commercial product RALLY=NOVA (myclobutanil) is used as an internal standard. Formulated myclobutanil 40 WP is applied at 100 and 20 ppm in water. Also included in the test is an inoculated control treatment (a water/acetone formulation blank).

D) Inoculation/Incubation—Treated vines are inoculated 24 hours after chemical application. Several diseased leaves are removed from inoculum production plants and are very gently brushed on the leaves of the test plants. This gentle contact and agitation allows spores to be dislodged from diseased leaves and fall onto test plant leaves.

The inoculation/incubation growth chamber is set at 24° C., 85% RH, and 12 hour photoperiod at 350 me/m$^2$/sec.

E) Evaluation—The test is rated 7–9 days after inoculation or upon maximum disease expression. Percent area infected with disease is determined for each replicate. Treatment means are calculated and percent disease control is determined by the formula "(control mean—treatment mean) * 100 / control mean". The untreated/inoculated control treatment is used for this calculation. The resultant percent protection or percent disease control for the compounds of the present invention is as set out in the Table below.

EXAMPLE 14

In Vitro Apple Scab Assay Methods (ASC—In Vitro) A)

A) Pathogen/Inoculum Production—A suspension of *Venturia inaequalis* conidia, adjusted to 150,000 spores/ml, is prepared using freshly harvested or frozen conidia. Apple seedlings, cv. McIntosh, are sprayed with this suspension and incubated in a high humidity chamber set at 20° C. with a 12 hour photoperiod for approximately four weeks. At maximum disease expression, a fine mist of deionized water is used to wash conidia from sporulating lesions and the resulting liquid/spore suspension is collected into glass vials and frozen at −80° C. for future use.

B) Compound Preparation—Water agar with 1.5% agar m/v is autoclaved to sterilization. Stock solutions of each compound of the present invention are made by solubilizing them in an appropriate solvent at a convenient concentration. Serial dilutions in solvent are made from this stock to execute the various test rates. When the molten agar is cool enough to pour, the compounds in solvent are dispensed into the agar such that the final concentration ratio of agar to solvent is 100:1. The agar is gently agitated and poured into petri plates, one plate per treatment. The standard used is 3-(difluoromethyl)-N- 2,3-dihydro-1,1,3-trimethyl-1H-inden-4-yl)-1-Methyl-1H-Pyrazole-4-carboxamide as found in U.S. Pat. No. 5,093,347.

C) Test Execution—Twenty-four hours after pouring, the plates are ready for inoculation. The previously collected frozen spore suspension is thawed at room temperature and diluted to a concentration of $1\times10^4$ spores/ml with sterile water. Three drops of approximately 0.1 ml each of the suspension are placed into each plate in an equidistant configuration. The plates are then placed in a dark incubator set at 20° C.

D) Test Evaluation—Forty to forty-eight hours later, the lengths of the spore germ tubes are measured using an ocular lens scale on a binocular microscope. Ten germ tubes in a drop are measured and an average determined for that drop. This procedure is repeated for the other two drops. The values for the three drops are then averaged to give the mean for the treatment. Percent inhibition of germination is calculated using the following equation: % Inhibition=(avg. control length—avg. treatment length/avg. control length) X 100.

The % inhibition values obtained from this assay for the compounds of the present invention are as set out in the Table below.

EXAMPLE 15

Apple Scab Foliar Assay Methods (ASC Prot)

A) Host Propagation—Apple, var. McIntosh, are collected form trees in the field and stored in a cold room at 4° C. After a minimum of 60 days storage, seed are collected and germinated in vermiculite in 3 inch pots in a growth chamber set at 27° C. day and 23° C. night temperature. When seedlings have emerged and 2–3 true leaves formed, the seedling are transplanted into 4 inch square pots containing a soil medium consisting of commercial potting mix. Seedlings are grown in this medium to the 8–10 leaf stage for use in tests. Before each test, the petiole of the smallest unfolded leaf is marked, with this leaf and the immediate five older leaves sprayed and inoculated in the test. The petiole of the oldest sprayed and inoculated leaf is also marked. The marking facilitates data collection for specific leaves and identification of the application site.

B) Test Compound Preparation—Compounds of the present invention are applied to the upper and lower leaf surfaces of the identified leaves at the rate of 100 and 20 ppm using a DiVilbiss Model 152 hand sprayer. Four plants per treatment are sprayed with 12 mls of spray solution which contains 40% acetone, 59.9% water, and 0.1% Triton B1956. Nova® (myclobutanil) is used as the commercial standard. It is suspended in water and applied at equivalent rates.

C) Pathogen/Inoculum Production—Inoculum from the apple scab pathogen, *Venturia inaequalis*, is obtained directly by washing conidia off of scab lesions from leaves on apple seedlings or by use of previously collected conidial suspension that has been frozen in a glass vial at −80° C. Conidial suspension concentration is adjusted to approximately $1\times10^5$ spores/ml by dilution with a solution of 1% v/v V8 juice/water. The conidial suspension is applied to the upper surface of the appropriate test leaves through a De Vilbiss atomizer set at 25 psi. Application of the suspension is continued until the entire leaf surface is covered uniformly with small droplets of inoculum. The inoculated plants are then moved into a mist chamber set at 20° C. with greater than 95% RH for 30 hours. Light intensity is 250 me/m²/ sec. After incubation in the mist chamber, the incubation period is continued in a growth chamber, same settings, no mist.

D) Test Evaluation—Phytotoxicity data, and leaf burning, etc. is collected by treatment at the time of pathogen inoculation and at disease evaluation. Disease is evaluated on day 8–12 by estimating the amount of treated leaf tissue that is covered by apple scab lesions or symptoms. Disease is rated using a modified Horsefal Barred scale. The percentage control is calculated as in the above examples. The results obtained from this assay for the compounds of the present invention are as set forth in the Table below.

EXAMPLE 16

Apple Scab Foliar Assay Methods (ASC Cur)—This assay is that of Example 1 except for the sequence of the chemical application and pathogen inoculation events. One month old apple seedlings are inoculated as described. 72 hours later, the plants are removed from the mist chamber and sprayed with the test chemicals and then returned to the mist-chamber after 1 to 2 hours. Disease evaluation is made on day 8–12.

The compounds of Examples 1–8 are combined with various adjuvants, carriers, and other additives and applied to vineyards at rates of from 0.01 to 2.0 kg active ingredient per hectare which reduce the incidence of Botrytis compared to untreated fields. The compounds in mixture with various adjuvants, carriers, and other additives are also applied to various vegetables and cereals at rates of from 0.01 to 2.0 kg active ingredient per hectare and reduce the incidence of fungal disease compared to untreated fields. The results of this assay for the compounds of the present invention are also as set out in the Table below.

TABLE

| | EXAMPLE 1 | EXAMPLE 2 | EXAMPLE 3 | EXAMPLE 4 |
|---|---|---|---|---|
| | | Compound | | |
| | BPM Prot | WPM Prot | WPM Cur | WES In vitro |
| | | Rates in ppm | | |
| | 500/100/20 | 500/100/20 | 100/20 | 5.0/0.5/0.1 |
| Number 1 | 88/—/— | | | 3/3/0 |
| Number 2 | 85/96/90 | —/65/44 | | 3/2/1 |
| Number 3 | —/98/98 | —/100*/77* | —/89 | 3/2/1 |
| Number 4 | | 100/91*/65* | | 3/2/1 |
| Number 5 | | 92/79*/52* | | 3/3/1 |
| Number 6 | | 98/—/— | | 2/0/0 |
| Number 7 | | 96/—/— | | 1/0/0 |
| Number 8 | | 91 (10 ppm) | | |

| | EXAMPLE 5 | EXAMPLE 6 | EXAMPLE 7 | EXAMPLE 8 |
|---|---|---|---|---|
| | | Compound | | |
| | WES Prot | WGB | WGB In Vitro | WGB Prot |
| | | Rates in ppm | | |
| | 500/100/20 | enzyme I-50 uM | 5.0/0.5/0.1 | 500/100/20 |
| Number 1 | 100/79*/29 | 0.015 | 3/3/0 | |
| Number 2 | —/82/12* | 0.037 | 2/1/0 | 99/86*/56* |
| Number 3 | —/95/01* | 0.05 | 0/0/0 | —/90*/79* |
| Number 4 | 100/98/54* | 0.029 | 2/1/1 | —/97/81* |
| Number 5 | —/99/59 | 0.008 | 2/2/0 | —/93/47 |
| Number 6 | 100/90/— | 0.52 | 1/0/0 | 89/86/70 |
| Number 7 | | 0.17 | 1/0/0 | |
| Number 8 | | | | 85 (10 ppm) |

| | EXAMPLE 9 | EXAMPLE 10 | EXAMPLE 11 | EXAMPLE 12 |
|---|---|---|---|---|
| | | Compound | | |
| | WGB Cur | WLR Prot | VGM Prot | VGM Cur |
| | | Rates in ppm | | |
| | 100/20 | 100/20 | 200/50/20 | 200/50/20 |
| Number 1 | | | 99/93/— | |
| Number 2 | | —/96 | 99/93*/90 | —/82/41 |
| Number 3 | 67*/62* | —/100 | —/87*/67* | —/90/84 |
| Number 4 | | | —/67*/41* | —/69/19 |
| Number 5 | | | | |
| Number 6 | | | | |
| Number 7 | | | | |
| Number 8 | | | | |

| | EXAMPLE 13 | EXAMPLE 14 | EXAMPLE 15 | EXAMPLE 16 |
|---|---|---|---|---|
| | | Compound | | |
| | VPM Prot | ASC In vitro | ASC Prot | ASC Cur |
| | | Rates in ppm | | |
| | 100/20/10 | 1.0/0.1 (A.I.) | 100/20 | 100/20 |
| Number 1 | | | | |
| Number 2 | 91/76/— | 3/3 | 99/58 | —/69 |
| Number 3 | —/51/34 | 3/3 | —/90 | |
| Number 4 | | | | |
| Number 5 | | | | |
| Number 6 | | | | |
| Number 7 | | | | |
| Number 8 | | | | |

AI = Activity Index
*Averaged value for more than one tests
the dash means rate not tested

| COMPOSITION EXAMPLES | Wt. Pct. |
|---|---|
| Suspension Concentrate: | |
| Compound of Example No. 1–8 | 48.900 |
| Polyoxypropylene-polyoxyethylene block copolymer | 2.550 |
| Sodium Lignin Sulfonate | 2.040 |
| 10% Dimethylpolysiloxane Emulsion | 1.020 |
| 1% Xanthan gum solution | 0.990 |
| Water | 44.500 |
| Emulsifiable Concentrate: | |
| Compound of each of Examples No. 1–8 | 13.5 |
| Ethoxylated sorbitan (20EO) | 5.0 |
| C9 Aromatics | 81.5 |
| Wettable Powder: | |
| Compound Example No. 1–8 | 75.0 |
| Sodium lignin sulfonate | 3.0 |
| Sodium N-methyl-N-oleyl-taurate | 1.0 |
| Kaolinite clay | 21.0 |
| Granule: | |
| Compound of Example No. 1–8 | 1.0 |
| Propylene glycol | 5.0 |
| Montmorillonite (24/48 mesh) | 94.0 |

| COMPOSITION EXAMPLES | Wt. Pct. |
|---|---|
| Dust: | |
| Compound of Example No. 8 | 50.0 |
| Graphite | 10.0 |
| Kaolinite clay | 40.0 |

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

We claim:

1. Compounds of the formula:

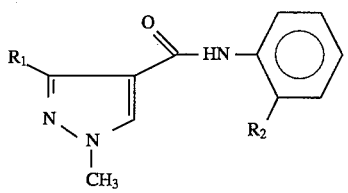

wherein:

$R_1$ is $CHF_2$ and $R_2$ is 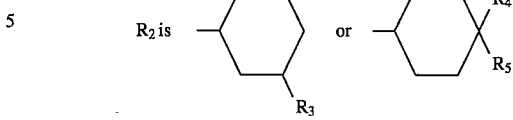

wherein $R_3$ is $CF_3$;

$R_4$ is $CF_3$; and $R_5$ is H or $CH_3$.

2. A compound of claim 1 which is 3-difluoromethyl-1-methyl-N-(2-( 3-trifluoromethyl)cyclohexyl)-phenyl )-1H-pyrazole-4-carboxamide.

3. A compound of claim 1 which is 3-difluoromethyl-1-methyl-N-(2-( 4-trifluoromethyl)cyclohexyl)phenyl)-1H-pyrazole-4-carboxamide.

4. Fungicidal compositions comprising a compound of claim 1 and an adjuvant.

5. A method of controlling fungal disease of a plant comprising applying a compound of claim 1 to the plant locus.

6. The method of claim 5 wherein said plant locus is the foliage of said plant.

7. The method of claim 5 wherein said plant locus is the seed of said plant.

* * * * *